(12) United States Patent
Yoo

(10) Patent No.: US 7,440,094 B2
(45) Date of Patent: Oct. 21, 2008

(54) OPTICAL SAMPLE CHARACTERIZATION SYSTEM

(75) Inventor: Woo Sik Yoo, Palo Alto, CA (US)

(73) Assignee: Wafermasters Incorporated, San Jose, CA (US)

( * ) Notice: Subject to any disclaimer, the term of this patent is extended or adjusted under 35 U.S.C. 154(b) by 169 days.

(21) Appl. No.: 11/291,246

(22) Filed: Nov. 30, 2005

(65) Prior Publication Data

US 2007/0121105 A1 May 31, 2007

(51) Int. Cl.
 *G01N 21/00* (2006.01)
(52) U.S. Cl. .................................. 356/237.5
(58) Field of Classification Search ......... 356/445–446, 356/237.1, 239.1, 239.3, 237.2–237.5
 See application file for complete search history.

(56) References Cited

U.S. PATENT DOCUMENTS

| | | | | |
|---|---|---|---|---|
| 3,879,131 | A * | 4/1975 | Cuthbert et al. | 356/521 |
| 3,964,830 | A * | 6/1976 | Ikeda et al. | 356/512 |
| 4,291,990 | A | 9/1981 | Takasu | |
| 5,264,912 | A * | 11/1993 | Vaught et al. | 356/237.5 |
| 6,137,570 | A | 10/2000 | Chung et al. | |
| 6,512,578 | B1 | 1/2003 | Komatsu et al. | |
| 2002/0122174 | A1 | 9/2002 | Hamamatsu et al. | |
| 2002/0140930 | A1 * | 10/2002 | Lin et al. | 356/237.2 |
| 2004/0233439 | A1 | 11/2004 | Mieher et al. | |

FOREIGN PATENT DOCUMENTS

WO   WO 00/00817   1/2000

* cited by examiner

*Primary Examiner*—Tarifur R Chowdhury
*Assistant Examiner*—Jonathon D Cook
(74) *Attorney, Agent, or Firm*—Tom Chen; MacPherson Kwok Chen & Heid, LLP.

(57) ABSTRACT

Systems and techniques for characterizing samples using optical techniques. Coherent light may be incident on a sample, and a diffraction pattern detected. Information indicative of diffraction pattern intensity may be used to determine one or more sample characteristics and/or one or more pattern characteristics. For example, sample characteristics such as stress, warpage, curvature, and contamination may be determined. The coherent light may be light of a single wavelength, or may be light of multiple wavelengths.

4 Claims, 4 Drawing Sheets

Warpage Contour Map

Curvature Vector Analysis Map

OPTICAL SAMPLE CHARACTERIZATION SYSTEM

BACKGROUND

1. Field of Invention

This invention generally relates to characterization of samples, particularly to optical systems for characterizing samples such as patterned and unpatterned semiconductor wafers.

2. Related Art

Optical techniques may be used to obtain information about materials. For example, optical techniques may be used to characterize substrates such as semiconductor wafers.

As the device density on wafers increases, it is more important to quickly obtain accurate information about the unpatterned (blanket) and patterned substrates. However, existing techniques may be time-consuming and cumbersome, and may not sample the wafer adequately. Additionally, some existing techniques are destructive; that is, they require that the wafer be damaged in order to analyze the patterned device elements. Therefore, characterization of actual product wafers may not be performed.

One technique that may be used to characterize patterned wafers is the inspection of patterns using a high magnification optical microscope, scanning electron microscope (SEM), or other imaging technique. However, these techniques may not provide a complete picture of the wafer patterns. Since a patterned wafer may contain millions or tens of millions of device elements (e.g., transistors), only a small percentage of the device elements may be characterized.

Another technique that may be used to characterize wafers is ellipsometry. Ellipsometry is an optical technique that measures the change in polarization as light is reflected off a surface. Although ellipsometry is an important tool for obtaining information about some sample characteristics (e.g., for measuring layer thickness and refractive index), it does not provide information about some other sample characteristics, such as stress and pattern integrity.

SUMMARY

Systems and techniques for characterizing samples (such as patterned and unpatterned substrates) to obtain sample information. The techniques may be used to quickly obtain information about sample characteristics such as sample curvature, warpage, stress, and contamination. For patterned samples, the techniques may provide pattern information as well as sample information.

In general, in one aspect, a sample characterization system includes a sample holder configured to position a sample to be characterized and a detection system positioned and configured to receive diffracted light from the sample. The diffracted light may comprise a first diffraction pattern corresponding to diffracted light of a first wavelength and a second diffraction pattern corresponding to diffracted light of a second different wavelength. The sample holder may be configured to move the sample relative to a probe beam The detection system may be further configured to generate a signal indicative of a first intensity of diffracted light corresponding to a first region of the sample surface at a first position of the detection system. The detection system may be further configured to generate a signal indicative of a second intensity of diffracted light corresponding to the first region of the sample surface at a second position of the detection system different than the first position.

The system may further include a processor configured to receive a signal indicative of the first intensity and the second intensity. The processor may be further configured to determine one or more sample surface characteristics of the first region of the sample surface using the signal indicative of the first intensity and the second intensity. The sample surface characteristics may include at least one of substrate stress, substrate warpage, substrate curvature, and substrate contamination.

The substrate may be a patterned substrate, and the processor may further be configured to determine one or more pattern characteristics of the first region of the sample surface. For example, the pattern characteristics may include pattern periodicity, pattern accuracy, pattern repeatability, pattern abruptness, pattern damage, pattern distortion, and pattern overlay.

The system may further include a coherent light source positioned to transmit light to be diffracted by the sample. The coherent light source may comprise a single wavelength source or a multiple wavelength source.

The detection system may comprise a screen positioned a distance from the sample holder, and may further comprise a camera positioned to receive light from the screen and to generate the signal indicative of the first intensity and the signal indicative of the second intensity. The camera may comprise at least one of a charge coupled device (CCD) camera, a complementary metal oxide semiconductor (CMOS) camera, and a photodiode detector array.

In general, in another aspect, an article comprises a machine-readable medium embodying information indicative of instructions that when performed by one or more machines result in operations comprising receiving information indicative of a first intensity of a diffraction pattern at a first position of a detection system, the diffraction pattern including light diffracted from a first region of a sample. The operations may further comprise receiving information indicative of a second intensity of the diffraction pattern at a second different position of the detection system. The operations may further comprise determining one or more sample surface characteristics of the first region of the sample using the data indicative of the first intensity and the data indicative of the second intensity. The operations may further comprise receiving information indicative of a different intensity of a different diffraction pattern at the first position of the detection system, wherein the different diffraction pattern includes light diffracted from a second different region of a sample.

In general, in another aspect, a method of sample characterization may comprise: receiving coherent light at a first region of a sample and detecting diffracted light from the first region of the sample at a detection system. The method may further comprise generating a signal indicative of a first intensity of the diffracted light corresponding to the first region at a first position of the detection system and generating a signal indicative of a second intensity of the diffracted light corresponding to the first region at a second different position of the detection system. The method may further comprise determining one or more sample surface characteristics based on the signal indicative of the first intensity and the signal indicative of the second intensity.

These and other features and advantages of the present invention will be more readily apparent from the detailed description of the exemplary implementations set forth below taken in conjunction with the accompanying drawings.

BRIEF DESCRIPTION OF THE DRAWINGS

Like reference symbols in the various drawings indicate like elements.

DETAILED DESCRIPTION

Systems and techniques provided herein may allow for efficient and accurate sample characterization. Both patterned and unpatterned wafers may be quickly characterized by analyzing diffraction patterns generated when coherent light is diffracted by a sample. Further, the techniques are non-destructive, so that actual product wafers may be characterized (if desired).

Figure 1:
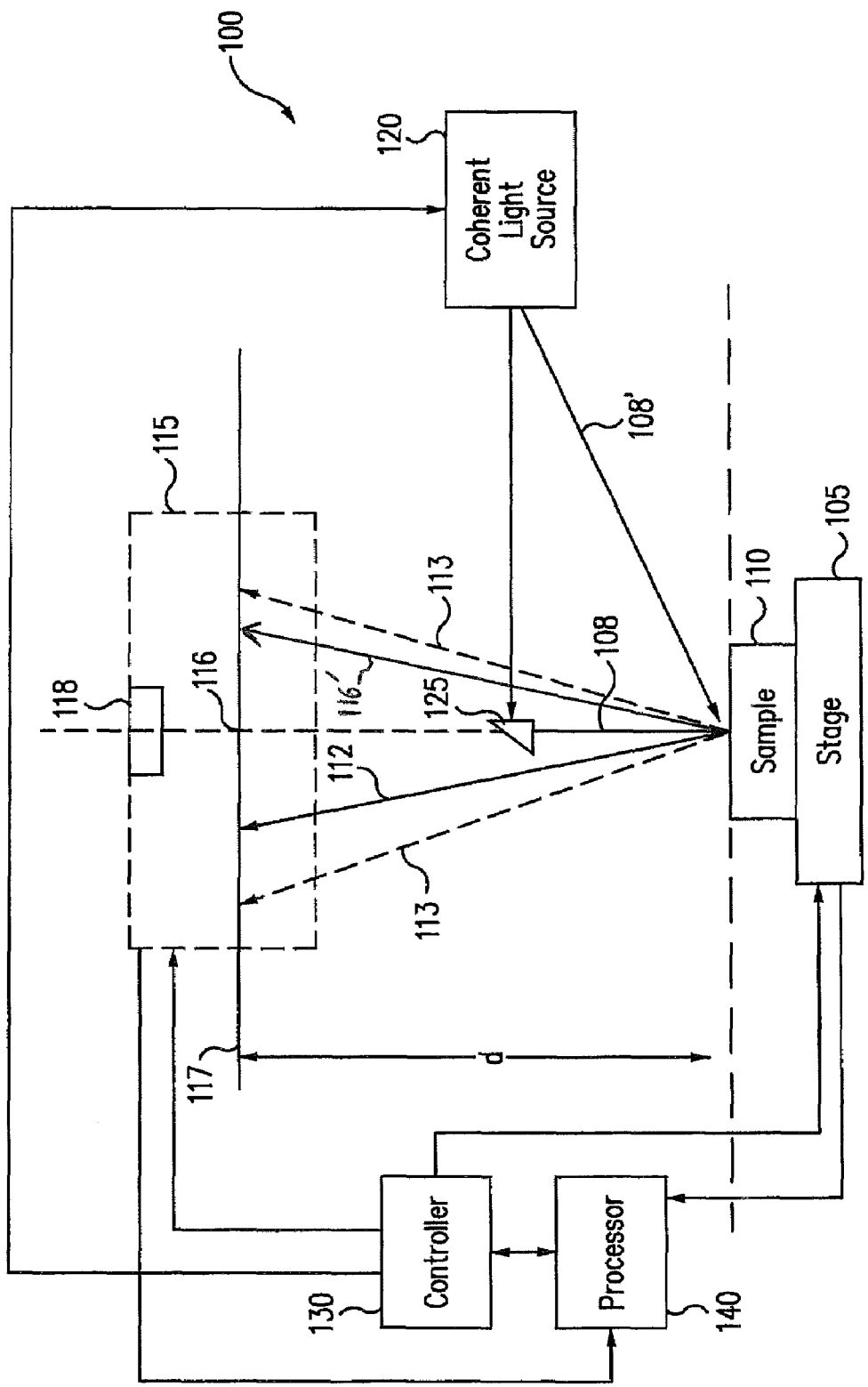
FIG. 1 is a schematic diagram of a sample characterization system, according to some embodiments.

FIG. 1 shows an embodiment of a system 100 configured to characterize a sample 110, such as a patterned or unpatterned semiconductor wafer. Light is generated by a coherent light source 120, and a probe beam 108 is directed to sample 110 using (for example) a prism 125.

Sample 110 may be mounted on a stage 105 so that relative movement between sample 110 and probe beam 108 may be provided. Stage 105 may be a translation and rotation stage (e.g., an X, Y, θ stage), that may comprise a goniometer. Probe beam 108, which may be about 0.1 µm (micrometer) to 10 mm in its major dimension (e.g., its diameter for a substantially circular beam), may be scanned across sample 110 to obtain data at a plurality of positions. For example, probe beam 108 may be raster scanned across sample 110 to obtain data for a "map" of sample characteristics. Note that one or more optical elements may be used to increase or decrease the size of probe beam 108 at sample 110. Smaller probe beams 108 may be used to obtain more detailed information about sample 110, while larger probe beams 108 may be used to characterize a wafer more quickly. This provides significant flexibility for different characterization applications.

In order to characterize sample 110, light is diffracted from sample 110 and a diffraction pattern is detected at a detection system 115 having a portion positioned a distance d from the surface. For example, detection system 115 may include a screen 117 positioned a distance d from sample 110, and a camera 118 (such as a CCD camera) positioned to receive light from screen 117 and to generate one or more signals indicative of the received light. The screen may detect reflected light 112 (the zeroth order diffraction maximum), as well as higher order diffracted beams 113 (e.g., light corresponding to first order diffraction maxima).

The example of FIG. 1 shows an embodiment in which light is incident on sample 110 normal to the ideal position of the surface of sample 110 (i.e., normal to a plane corresponding to the ideal position of the surface). If the surface of sample 110 is not flat in the region sampled by the incident light, the reflected beam 112 will intersect screen 117 at a position 116' offset from an ideal position 116. The offset may be referred to as the warpage vector.

Light may also be incident on the surface of sample 110 specularly (i.e., at an angle other than perpendicular to the expected position of the surface of sample 110, as indicated with probe beam 108'). For such embodiments, detection system 115 may have a portion positioned to receive diffracted light from sample 110. Sample surface characteristics and/or pattern characteristics may be calculated using techniques that account for the particular angle of incidence used.

Figure 2A:
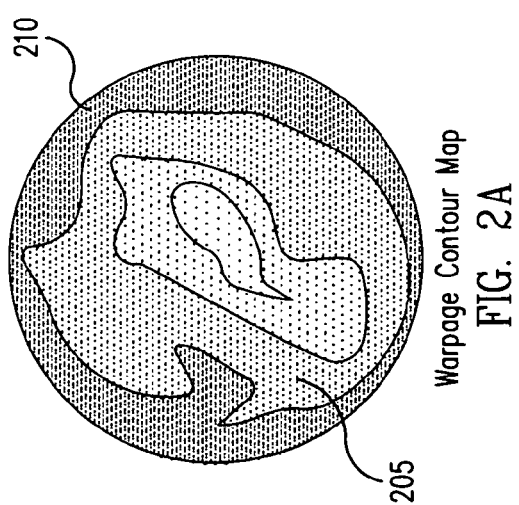
FIG. 2A is a warpage contour map that may be obtained using a system such as the system of FIG. 1.
Figure 2B:
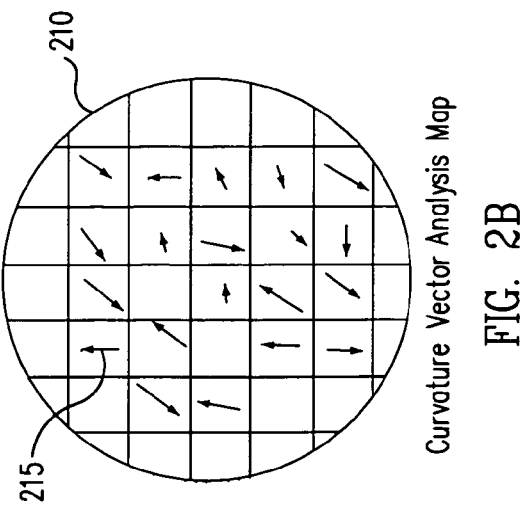
FIG. 2B is a curvature vector analysis map that may be obtained using a system such as the system of FIG. 1.

When sample 110 comprises an unpatterned wafer, the resulting diffraction pattern may be indicative of sample surface characteristics such as wafer warpage, curvature, global and local stress, and may indicate the presence of contaminants (e.g., particles). The detected signal may be used to characterize the unpatterned wafer in a number of ways. For example, FIG. 2A shows a warpage contour map 205 of a sample 210 (such as an unpatterned wafer). FIG. 2B shows a curvature vector analysis map 215 of sample 210.

When sample 110 is a patterned wafer, the resulting diffraction pattern is indicative not only of wafer warpage and stress, but also of pattern characteristics. System 100 may provide large area pattern integrity characterization by reverse Fourier transform of the diffracted image to obtain pattern information. For example, information indicative of periodicity, pattern accuracy, pattern repeatability, pattern abruptness, pattern damage, pattern distortion, and pattern overlay may be obtained.

System 100 may further include one or more controllers such as a controller 130, and one or more processors such as a processor 140. Controller 130 may control stage 105, light source 120, and/or detection system 115. First example, controller 130 may control stage 105 to position sample 110 so that probe beam 108 is sampling a first region at a first time, and may control detection system 115 to obtain data at the first time. At a second later time, controller 130 may control stage 105 to position sample 110 so that probe beam 108 is sampling a second different region at a second later time, and may control detection system 115 to obtain data at the second later time. Controller 130 may control light source 120 to select one or more particular wavelengths, or to control other parameters.

Processor 140 may receive information indicative of a position on sample 110 being characterized at a particular time, and may also receive information indicative of an intensity of a diffraction pattern at different positions of detection system 115 at the particular time. Processor 140 may determine sample characteristics (such as wafer characteristics and/or pattern characteristics) using the received information.

A system such as system 100 of FIG. 1 may provide fast, accurate, and flexible characterization of a sample. For example, the beam size may be tailored to sample a desired area at a particular time. Additionally, the distance d between the sample and the detection system may be increased or decreased to increase or decrease the effective magnification, as well as to improve resolution.

Additional benefits may be obtained by characterizing the sample using multiple wavelengths of coherent light. For diffractive elements separated by a distance d being illuminated by light of wavelength λ at an angle θ, the diffraction condition is nλ=2 d sin θ (where n is the diffraction order). Because the diffraction condition is dependent on both pattern size and wavelength, different wavelengths of light will interact differently with different patterns.

Figure 3:
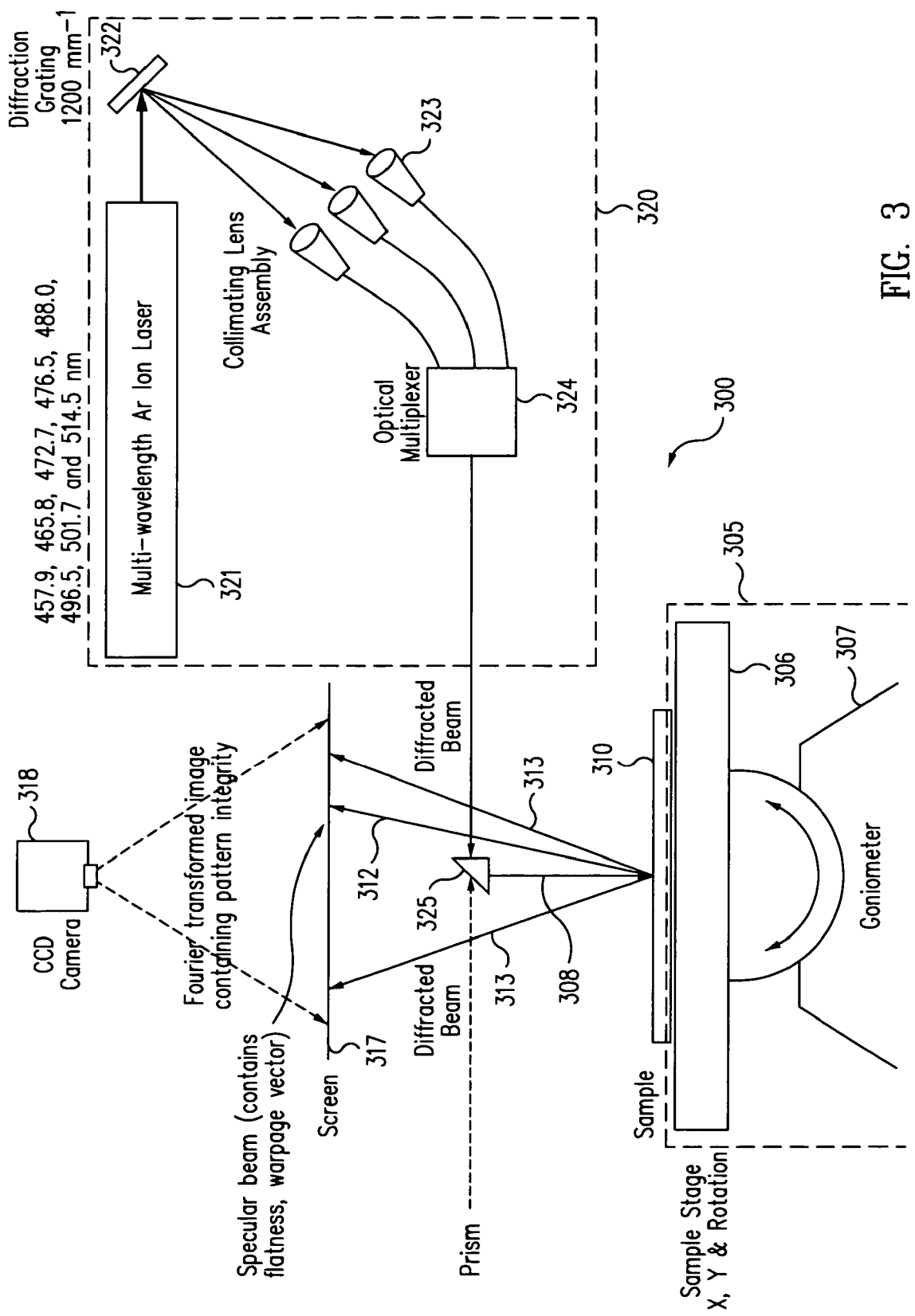
FIG. 3 is a schematic diagram of a sample characterization system, according to some embodiments.

FIG. 3 shows a system 300 configured to generate a probe beam 308 including a plurality of wavelengths, that may be used to characterize a sample 310 such as a semiconductor wafer. A coherent light source 320 includes one or more lasers such as multi-wavelength argon ion laser 321, to generate coherent light of at least two different wavelengths. For example, an argon ion laser can generate light having wavelengths of 457.9, 465.8, 472.7, 476.5, 488.0, 496.5, 501.7, and 514.5 nm. Although FIG. 3 shows a single laser generating multiple wavelengths, multiple lasers may be used.

The light may be dispersed according to wavelength using a dispersive element such as a diffraction grating 322 (e.g., a 1200 mm$^{-1}$ grating). Each of the wavelengths of the dispersed light may be collimated using a collimating lens assembly 232, and then multiplexed using an optical multiplexer 324. The resulting light may be directed to sample 310 using one or more elements such as a prism 325. As noted above, light may be directed to sample 310 at normal incidence, or may be directed to sample 310 specularly.

In the example of FIG. 3, stage 305 comprises an XY translation stage 306 and a goniometer 307 configured to provide measured rotation to sample 310. Stage 305 may be controlled using a controller (e.g., an integrated stage controller and/or a system controller, not shown).

Probe beam 308 is diffracted by sample 310, generating a specular beam 312 and diffracted beams 313. Beams 312 and 313 are received at a screen 317. The diffraction patterned is a Fourier transformed image of the pattern that contains pattern information.

A camera 318 (such as a charge coupled device or CCD camera, a complementary metal oxide semiconductor or CMOS camera, or photodiode array camera) receives light from screen 317 and generates signals indicative of the intensity of the diffraction pattern at positions on screen 317. The signals indicative of the diffraction pattern may be received by a processor, which may determine one or more sample characteristics based on the signals.

For multiple incident wavelengths, camera 318 may be a wavelength-sensitive camera, such as a color CCD camera. As noted above, different wavelengths are more sensitive to pattern features of particular sizes. As a result, a first wavelength may provide more complete information about some pattern features, while a second, different wavelength may provide more complete information about different pattern features. Thus, using multiple wavelengths may provide a special benefit for samples in which different feature sizes are of interest.

Figure 4:
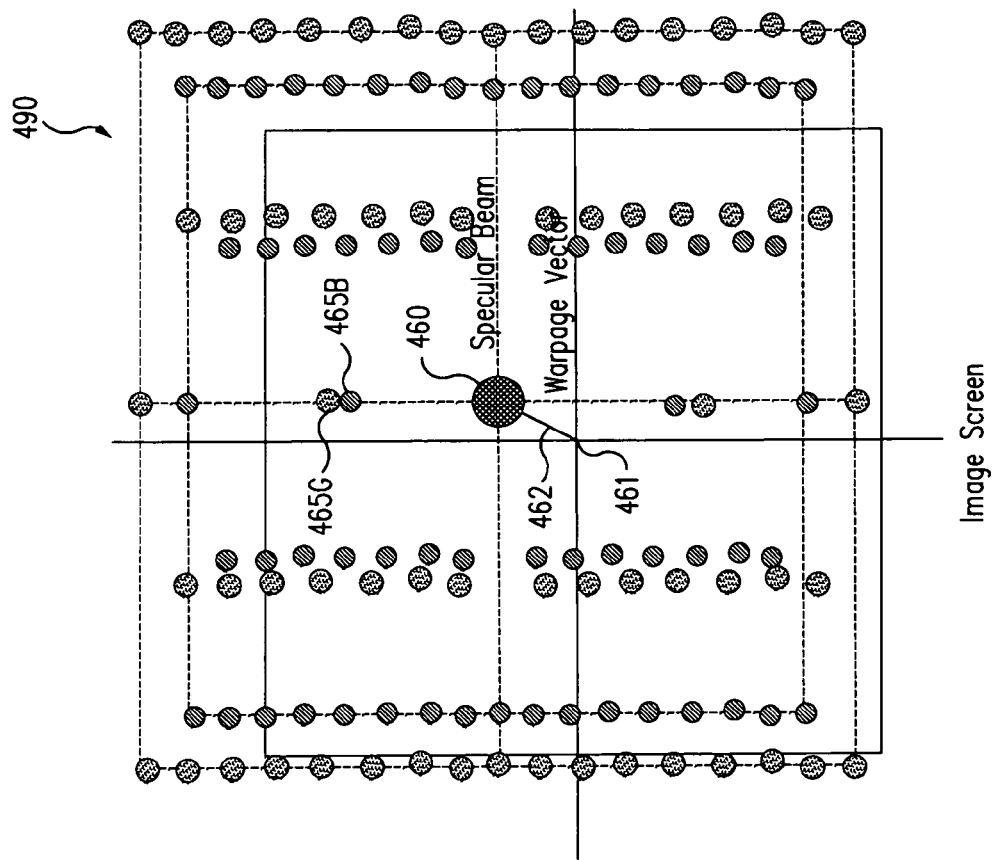
FIG. 4 is a diffraction pattern that may be obtained using a system such as the system of FIG. 3.

FIG. 4 shows a diffraction pattern 490 that may be obtained using a system such as system 300 of FIG. 3, with blue and green incident light. Blue light has a shorter wavelength, and so the diffraction maxima corresponding to diffracted blue light are closer together than the diffraction maxima corresponding to diffracted green light. In FIG. 4, the diffraction maximum 460 corresponding to specular beam 312 is displaced from the ideal position 461 by a warpage vector 462. Ideal position 461 is the position at which specular beam 312 would be detected in the absence of warpage at the region of the sample being characterized at the particular time. Diffraction pattern 490 further includes a number of intensity maxima, such as spots 465B (corresponding to incident blue light) and 465G (corresponding to incident green light).

Figure 5:
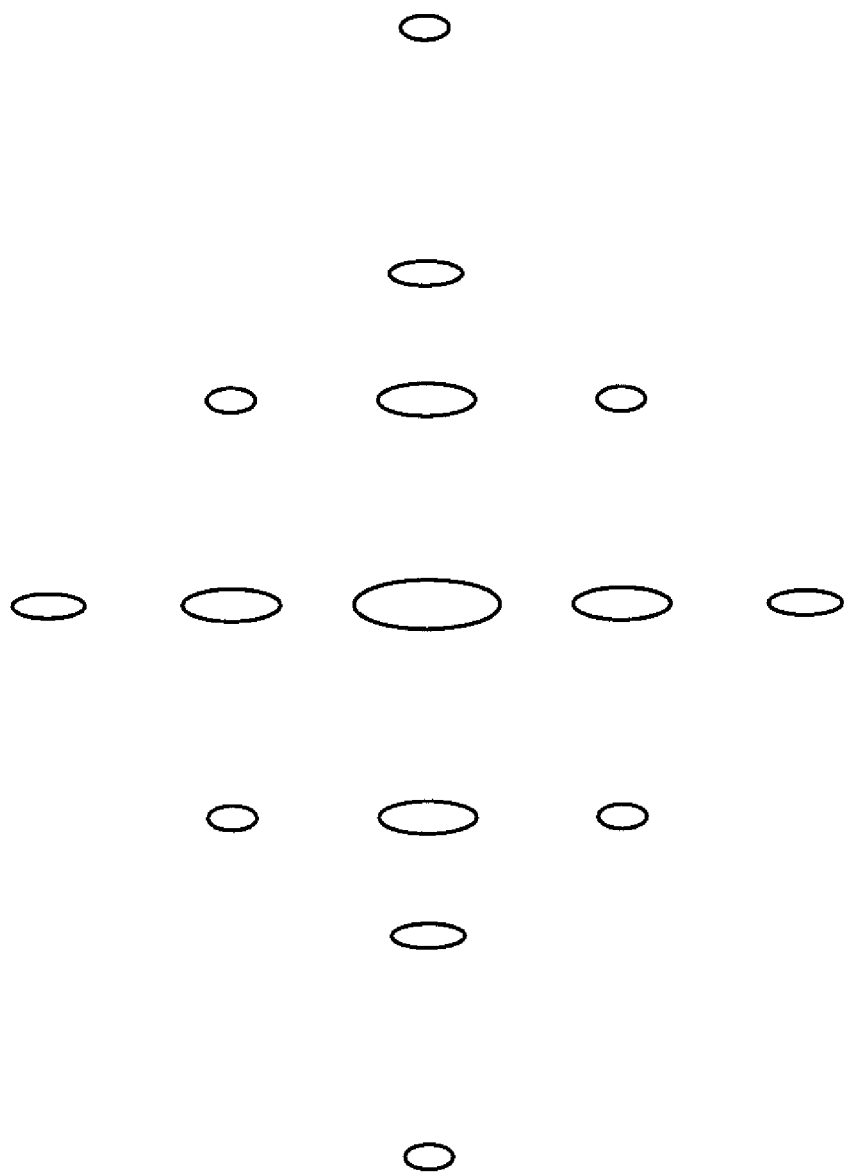
FIG. 5 is a diffraction pattern of a patterned sample obtained using a laser light source.

For a "perfect" sample in the region being sampled by the probe beam, the diffraction maxima would form an array of spots with sharp edges, where the positions of the spots may be calculated using the wavelength of light and sample parameters. However, for a flawed sample, the boundaries of the spots may blur, and their positions may deviate from the calculated position. Since the spatial intensity variation of the diffraction pattern is the Fourier transform of the diffracting structure, intensity information may be obtained using detection system 315, and an inverse Fourier transform performed. The result of the inverse Fourier transform may be compared to a result for an ideal sample and/or pattern, to determine sample characteristics. Alternately, the intensity variation for an ideal sample may be determined (e.g., by Fourier transforming the ideal sample and/or pattern) and compared to the obtained intensity data. FIG. 5 shows an exemplary illustration of a diffraction pattern for a patterned wafer illuminated by a laser pointer. The blurring of the diffractions spots indicates that it is an imperfect sample. The contrast between spots and spotless regions tells us the pattern integrity (periodicity and/or regularity).

In implementations, the above described techniques and their variations may be implemented at least partially as computer software instructions. Such instructions may be stored on one or more machine-readable storage media or devices and are executed by, e.g., one or more computer processors, or cause the machine, to perform the described functions and operations.

A number of implementations have been described. Although only a few implementations have been disclosed in detail above, other modifications are possible, and this disclosure is intended to cover all such modifications, and most particularly, any modification which might be predictable to a person having ordinary skill in the art. For example, the incident light may be transmitted to the sample in a number of different ways (e.g., using fewer, more, and/or different optical elements than those illustrated). Furthermore, relative motion between the sample and the probe beam may be provided by moving the sample (as shown), by moving the probe beam, or both. For example, at least part of the optical system may be configured to scan the probe beam across a fixed sample.

Additionally, rather than a single controller, multiple controllers may be used. For example, a stage controller and separate detection system controller may be used. Controllers may be at least partially separate from other system elements, or may be integrated with one or more system elements (e.g., a stage controller may be integrated with a stage). Additionally, multiple processors may be used, and may include signal processors and/or data processors.

Also, only those claims which use the word "means" are intended to be interpreted under 35 USC 112, sixth paragraph. Moreover, no limitations from the specification are intended to be read into any claims, unless those limitations are expressly included in the claims. Accordingly, other embodiments are within the scope of the following claims.

What is claimed is:

1. A sample characterization system comprising:
   a sample holder configured to position a sample to be characterized;
   a multi-wavelength coherent light source;
   a diffraction grating configured to receive light from the multi-wavelength coherent light source and to diffract the received light into a plurality of diffracted beams, each diffracted beam having a unique wavelength;
   a plurality of collimators corresponding to the plurality of diffracted beams, each collimator being configured to receive a corresponding diffracted beam and to convert the corresponding diffracted beam into a collimated beam;
   an optical multiplexer configured to receive the collimated beams from the plurality of collimators so as to illuminate a portion of the sample with a multiplexed beam, the sample being positioned by the sample holder so as to reflect a diffraction pattern onto an inspection screen, the diffraction pattern being a composite of diffraction maxima in each of the unique wavelengths;

a detection system positioned to image the diffraction pattern; and a processor configured to inverse Fourier transform the diffraction pattern imaged by the detection system to determine sample surface characteristics of the illuminated portion, the sample holder being controlled to move the sample so that multiple portions of the sample are characterized.

2. The system of claim 1, wherein the detection system includes a camera that comprises at least one of a charge coupled device (CCD) camera, a complementary metal oxide semiconductor (CMOS) camera, and a photodiode detector array.

3. The system of claim 1, wherein the sample surface characteristics comprise at least one of substrate stress, substrate warpage, substrate curvature, and substrate contamination.

4. The system of claim 1, wherein the sample holder is a translation and rotation stage.

* * * * *